ROSE PLANT
Filed Oct. 26, 1967 2 Sheets-Sheet 1
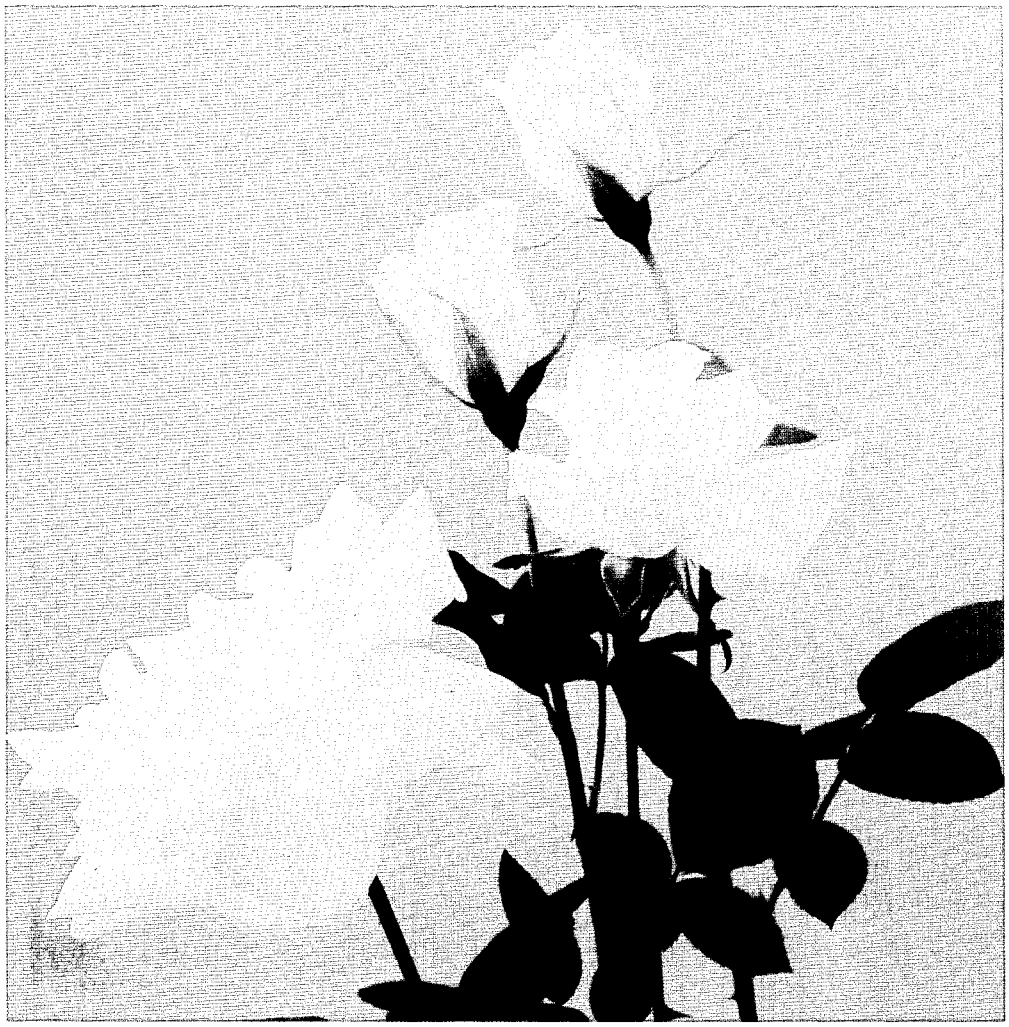

ROSE PLANT
Filed Oct. 26, 1967 2 Sheets-Sheet 2
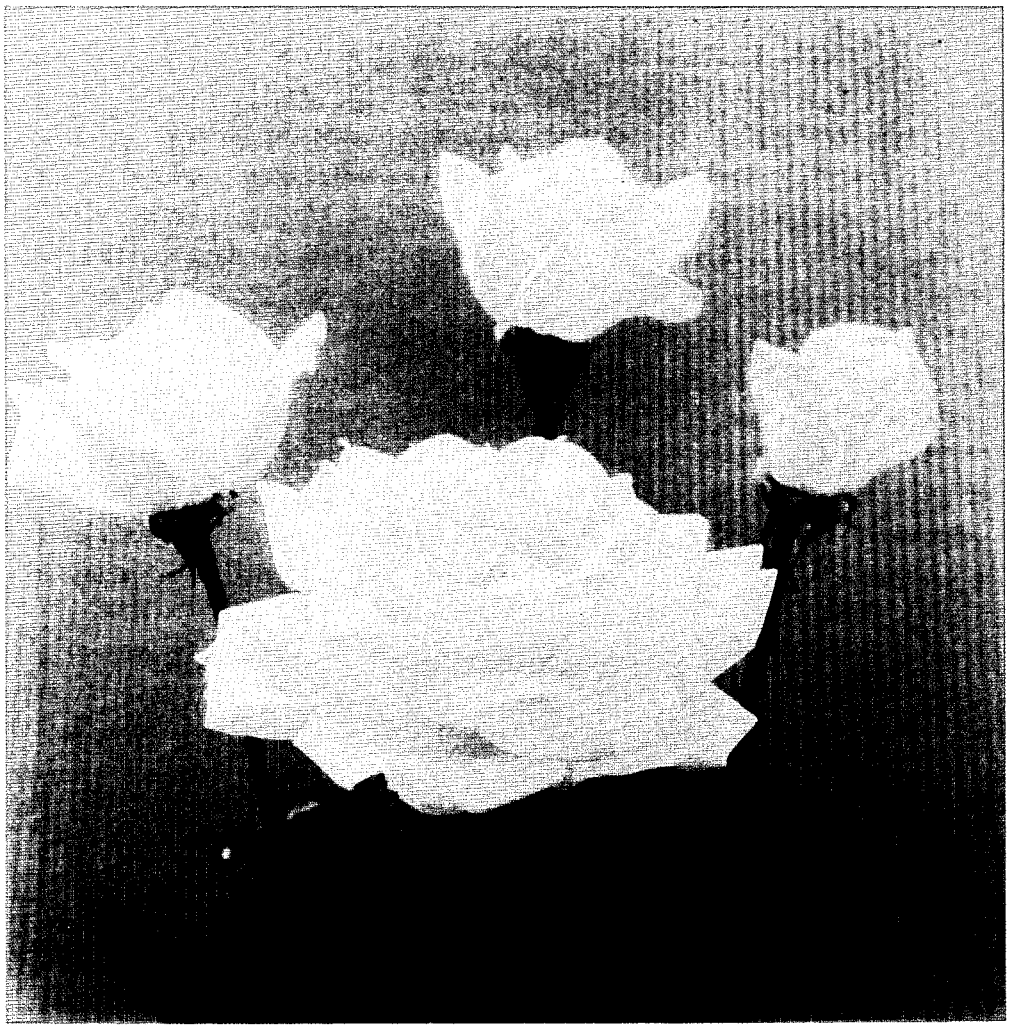

United States Patent Office

Plant Pat. 2,947
Patented Dec. 9, 1969

2,947
ROSE PLANT

Dennison H. Morey, Jr., 2750 Fulton Road,
Santa Rosa, Calif. 95404

Filed Oct. 26, 1967, Ser. No. 678,465
Int. Cl. A01h 5/02
U.S. Cl. Plt.—15 1 Claim The invention relates to a new and distinct variety of rose plant of the hybrid tea class originated by me in 1953 as a consequence of a breeding program begun in 1951. The parentage of my new rose plant is as follows: Joanna Hill × Elinor Le Grice.

The object of the cross was to obtain a cadmium yellow, fragrant hybrid tea with a high degree of disease resistance, profuse early flowering and rapid succession of bloom. These objectives were achieved along with other desirable improvements, as evidenced by the following unique combination of characteristics which are outstanding in the new variety and which distinguish it from its parents as well as from all other varieties of which I am aware. My new variety is primarily characterized by: precocious flowering, profuse early season bloom, intense fragrance, disease resistant foliage, buff yellow color and the full high centered decorative flowers.

Asexual reproduction of my new variety by budding, through a series of annual propagations at Livermore and, Ontario, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following bontanical description is based upon observation of field and container grown budded plants under greenhouse and field conditions at Livermore and Ontario, Calif.

Moderate to abundant foliage, odd pinnate, smooth, leathery, very glossy. 5 to 3 leaflets below flower. Terminal leaflet generally obovate, otherwise generally ovate with pointed tip and serrated margins, 1½" wide x 2¼" long to 2¼" wide x 3½" long. Young leaflets Willow Green (HCC 000862) on upper surface; Parsely Green (HCC 00962/3) below: mature leaves Ivy Green (HCC 0001060/1) upper, Spinach Green (HCC 0960) below. Petioles ½ to 1" long; ribs and veins conspicuous.

Thorns 3 to 7 per 3" stem. 1/16"–7/16" tall; 1/16"–3/16" wide; ⅛"–7/16" long. The thorns are reddish pink at base fading to straw at tip when young. Silver with pinkish tan blush when old. Some prickles scattered among thorns, none on peduncle. Few small (⅛" or less) hooked thorns on rachis; hooked point coming below center.

The flower bud is large, pointed becoming urceolate of medium size, 1⅛"–1½" long, ⅝"–¾" wide, opens slowly. The bud color is Peach (HCC 512/1–512) when sepals first divide and begin to unfurl. Sepals moderately appendaged, do not curl back as they unfurl. Branched. They are Lavender Green (HCC 000761/1) inside and Spinach Green (HCC 0960/1) outside. Hypanthium is funnel form of medium size, ½" wide x ¼" long, outside smooth, inside hairy. The peduncle is strong, erect with no prickles, 3⅛"–3¾", Lettuce Green (HCC 861/1).

Blooming habit recurrent, intermittent, but nearly continuous. Plant blooms heavily from spring through fall. Blooms borne singly on moderately strong canes. Medium sized flowers 4–4¾" in diameter, 1½"–2" in depth; high centered when bloom first opens, flattens and becomes somewhat cup shaped as bloom matures. Petals imbricated, 25–30 waxey and silky, reminiscent of a wet chamois, obovate. Outside petal is Aureolin (HCC–3) at base becoming Aureolin (HCC 3/3); inside petal is Canary Yellow (HCC 2/1) at base becoming Mimosa Yellow (HCC 602/1). Inner reverse side Aureolin (HCC 3/1) at base becoming Salmon (HCC 412) at margin and ½" inwards. Outer reverse side Aureolin (HCC 3/2) at base becoming Salmon (HCC 412) at margin inwards. After full bloom fades to Aureolin (HCC 3/3). Petals are 1⅜"–2" wide, 1¾"–2" long. Petaloids (staminoids) 10–15, ¾"–1½" long; ¼"–⅝" wide, color like petals, but somewhat streaked with Salmon (HCC 412). Very strong fragrance, reminiscent of citronella and jasmin.

As illustrated, the intense yellow develops under moderate temperatures with abundant sunlight, while lighter colors develop during warmer temperatures and foggy periods.

The ovaries are ordinary. The variety is infertile. Stamens and anthers plus or minus 130 in number ½–1" in length, whorled arrangements. Filaments 5/16–13/16" long, yellow in color, orange pollen. Pistils plus or minus 85 in number, plus or minus 5/16" in length. Style magenta.

Having thus disclosed my invention, I claim:

1. A new and distinct variety of rose plant of the hybrid tea class substantially as herein shown and described primarily characterized by: precocious flowering, profuse early season bloom, intense fragrance, disease resistant foliage, buff yellow color and the full high centered decorative flowers.

No references cited.

ROBERT E. BAGWILL, Primary Examiner